(12) United States Patent
Peled et al.

(10) Patent No.: US 11,547,391 B2
(45) Date of Patent: Jan. 10, 2023

(54) ACOUSTIC PHANTOM AND METHOD FOR INTRACARDIAC ULTRASOUND LOCALIZATION CATHETER

(71) Applicant: Biosense Webster (Israel) Ltd., Yokneam (IL)

(72) Inventors: Ran Peled, M.P. Misgav (IL); Eid Adawi, Tur'an (IL); Fares Safe, Yanuh (IL); Michael Berger, Haifa (IL); Tal Yehezkel, Pardes Hanna (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 1066 days.

(21) Appl. No.: 16/123,012

(22) Filed: Sep. 6, 2018

(65) Prior Publication Data

US 2019/0380687 A1    Dec. 19, 2019

Related U.S. Application Data

(60) Provisional application No. 62/684,942, filed on Jun. 14, 2018.

(51) Int. Cl.
*A61B 8/12* (2006.01)
*A61B 8/00* (2006.01)
(Continued)

(52) U.S. Cl.
CPC ............... *A61B 8/587* (2013.01); *A61B 8/12* (2013.01); *A61B 8/4254* (2013.01); *G01S 7/5205* (2013.01); *A61B 8/4272* (2013.01); *A61B 8/445* (2013.01); *A61B 8/4488* (2013.01); *A61B 8/488* (2013.01)

(58) Field of Classification Search
CPC ......... A61B 8/587; A61B 8/4494; A61B 8/12; A61B 8/4254; A61B 8/4272; A61B 8/445; A61B 8/4488; A61B 8/488; A61B 5/062; A61B 8/0891; G01S 7/5205
See application file for complete search history.

(56) References Cited

U.S. PATENT DOCUMENTS 6,192,735 B1    2/2001  Nagai
6,266,551 B1    7/2001  Osadchy et al.
(Continued)

FOREIGN PATENT DOCUMENTS

WO    9605768 A1    2/1996

OTHER PUBLICATIONS

Tobis et al., "Intravascular Ultrasound Cross-Sectional Arterial Imaging Before and After Balloon Angioplasty In Vitro", Oct. 1989, pp. 873-882 (Year: 1989).*

(Continued)

*Primary Examiner* — Patricia J Park
*Assistant Examiner* — Adil Partap S Virk
(74) *Attorney, Agent, or Firm* — Notaro, Michalos & Zaccaria P.C.

(57) ABSTRACT

Apparatus for calibration includes a mount and one or more acoustic targets. The mount, which is adapted to hold a medical probe, includes an acoustic imaging device that emits ultrasonic beam in a plane, while permitting an orientation of the plane of the ultrasonic beam to be adjusted. The one or more acoustic targets are arranged to continuously intersect the plane of the ultrasonic beam over a given range of orientation angles.

7 Claims, 4 Drawing Sheets

(51) Int. Cl.
    *G01S 7/52* (2006.01)
    *A61B 8/08* (2006.01)

(56) References Cited

U.S. PATENT DOCUMENTS

| | | | |
|---|---|---|---|
| 6,690,963 B2 | 2/2004 | Ben-Haim et al. | |
| 6,716,166 B2 | 4/2004 | Govari | |
| 6,773,402 B2 | 8/2004 | Govari et al. | |
| 6,775,404 B1 | 8/2004 | Pagoulatos et al. | |
| 7,090,639 B2 | 8/2006 | Govari | |
| 7,735,349 B2 | 6/2010 | Hochmitz | |
| 7,874,987 B2 | 1/2011 | Altmann et al. | |
| 7,996,057 B2 | 8/2011 | Govari et al. | |
| 9,468,422 B2 | 10/2016 | Hyun et al. | |
| 2003/0122544 A1* | 7/2003 | Parker | A61B 6/583 324/309 |
| 2006/0122506 A1* | 6/2006 | Davies | G01S 7/52046 600/437 |
| 2006/0241445 A1* | 10/2006 | Altmann | A61B 8/12 600/443 |
| 2007/0106156 A1 | 5/2007 | Altmann et al. | |
| 2008/0183075 A1* | 7/2008 | Govari | A61B 8/12 600/437 |
| 2008/0287787 A1* | 11/2008 | Sauer | A61B 5/062 600/437 |
| 2012/0277585 A1* | 11/2012 | Koenig | A61B 8/58 600/437 |
| 2013/0139567 A1* | 6/2013 | Madsen | G01N 29/30 73/1.86 |
| 2013/0338498 A1* | 12/2013 | Emelianov | A61B 5/0084 600/431 |
| 2014/0121501 A1* | 5/2014 | Fichtinger | A61B 8/4209 600/424 |
| 2016/0133159 A1* | 5/2016 | Saloux | G09B 23/32 73/866.4 |
| 2018/0000460 A1* | 1/2018 | Lepage | G01S 15/89 |
| 2018/0035970 A1* | 2/2018 | Avila | A61B 5/055 |
| 2018/0132821 A1 | 5/2018 | Dehghan Marvast et al. | |

OTHER PUBLICATIONS

Zhou et al., "Review of Advanced Catheter Technologies in Radiation Oncology Brachytherapy Procedures", Jul. 16, 2015, Cancer Management and Research, pp. 199-211 (Year: 2015).*
Extended European Search Report for corresponding European patent application No. 19179888.3, dated Oct. 8, 2019.
Pending U.S. Appl. No. 15/792,404, filed Oct. 24, 2017.
Weisstein, Eric W. "Closed Curve." From MathWorld—A Wolfram Web Resource. https://mathworld.wolfram.com/ClosedCurve.html, retrieved Oct. 18, 2022.

* cited by examiner

ACOUSTIC PHANTOM AND METHOD FOR INTRACARDIAC ULTRASOUND LOCALIZATION CATHETER

CROSS-REFERENCE TO RELATED APPLICATIONS

This application claims the benefit of U.S. Provisional Patent Application 62/684,942, filed Jun. 14, 2018, whose disclosure is incorporated herein by reference.

FIELD OF THE INVENTION

The present invention relates generally to the calibration of medical probes, and particularly to calibration of intracardiac ultrasound probes.

BACKGROUND OF THE INVENTION

Invasive ultrasound imaging of cardiac cavities is a known diagnostic technique, which requires calibration to produce reliable images. For example, U.S. Pat. No. 7,996,057 describes an apparatus that has a rigid mechanical framework, for calibration of a probe that includes a magnetic position sensor and an acoustic imaging device. One or more field generators, fixed to the framework, generate a magnetic field of known spatial characteristics. An acoustic target assembly includes a phantom coupled to a motion mechanism, which is arranged to move the phantom in a known orbit relative to the framework. A jig, fixed to the framework, holds the probe within the magnetic field of the one or more field generators, in an orientation suitable for the imaging device to image the phantom. A processor processes position and image signals from the probe in order to calibrate coordinates of the imaging device relative to the position sensor.

As another example, U.S. Pat. No. 9,468,422 describes a sensor coupled to an ultrasound probe, which provides position information related to an ultrasound imaging position in an object. A processor performs first registration between the medical image and the ultrasound image, which provides a relationship between a coordinate system of the medical image and a coordinate system of the ultrasound image. That way, the processor obtains first registration information based on the first registration. The processor performs second registration between the sensor and the medical image based on the position information and the first registration information, and obtains second registration information based on the second registration.

U.S. Pat. No. 7,090,639 describes an apparatus for calibrating a probe having a position sensor and an ultrasonic transducer. The apparatus includes a test fixture, which includes an ultrasonic target disposed therein at a known position. A computer is adapted to receive a position signal generated by the position sensor while the transducer is in alignment with the ultrasonic target, determine an orientation of the probe in a frame of reference of the test fixture, and determine calibration data for the probe responsive to the orientation of the probe.

U.S. Pat. No. 6,192,735 describes a probe fixed to a calibrator body, wherein the calibrator body is mounted on a base stand. With the surfaces thereof abutted against a block, the probe is positioned in X-axis, Y-axis and Z-axis directions. Under this condition, image data is calibrated which is provided with the aid of an ultrasonic wave generated by the probe according to the spatial position data of a magnetic field receiver. In an embodiment, the probe is adapted to transmit and receive an ultrasonic wave generated by an ultrasonic diagnostic equipment is set in triaxial directions, the spatial position coordinate of a magnetic field receiver which is mounted on the probe and receives a magnetic field, is detected, and the spatial position of the echo image of an object under test, which is provided by the ultrasonic diagnostic equipment, is corrected so that a correct three-dimensional image is formed again.

U.S. Pat. No. 7,735,349 describes a calibration apparatus that includes a motion assembly, which is arranged to move an imaging probe through a calibration point having known coordinates. The imaging probe includes an ultrasound transducer and a position sensor for acquiring concurrently a first sequence of ultrasound images and a second sequence of position measurements. The apparatus further includes a marking circuit, which is arranged to mark an ultrasound image that is acquired by the ultrasound transducer in the first sequence when the imaging probe is at the calibration point. A processor is arranged to calibrate a time offset between the first and second sequences by associating the marked ultrasound image in the first sequence with a position measurement in the second sequence whose coordinates match the coordinates of the calibration point.

SUMMARY OF THE INVENTION

An embodiment of the present invention provides an apparatus for calibration including a mount and one or more acoustic targets. The mount, which is adapted to hold a medical probe, includes an acoustic imaging device that emits ultrasonic beam in a plane, while permitting an orientation of the plane of the ultrasonic beam to be adjusted. The one or more acoustic targets are arranged to continuously intersect the plane of the ultrasonic beam over a given range of orientation angles.

In some embodiments, the one or more of the acoustic targets are shaped as arcs.

In some embodiments, each of the arcs is one of orthogonal to the plane of the ultrasonic beam and slanted with respect to the plane of the ultrasonic beam.

In an embodiment, the mount and the acoustic targets are entirely non-ferromagnetic.

In another embodiment, the acoustic targets include intermittent acoustic targets.

In some embodiments, the probe includes a magnetic position sensor, and wherein the apparatus includes a position sensor calibration setup, which is adapted to determine, based on readings of the position sensor, a physical displacement along a longitudinal axis of the probe between the magnetic sensor and the acoustic imaging device.

There is additionally provided, in accordance with an embodiment of the present invention, a method for producing a calibration apparatus, the method including providing a mount, which is adapted to hold a medical probe, which includes an acoustic imaging device that emits ultrasonic beam in a plane, while permitting an orientation of the plane of the ultrasonic beam to be adjusted. One or more acoustic targets, which are arranged to continuously intersect the plane of the ultrasonic beam over a given range of orientation angles, are coupled to the mount.

There is additionally provided, in accordance with an embodiment of the present invention, a method for calibration including holding a medical probe, which includes an acoustic imaging device that emits ultrasonic beam in a plane, in a mount, while permitting an orientation of the plane of the ultrasonic beam to be adjusted. The acoustic imaging device is calibrated using one or more acoustic targets, which are arranged to continuously intersect the plane of the ultrasonic beam over a given range of orientation angles.

The present invention will be more fully understood from the following detailed description of the embodiments thereof, taken together with the drawings in which:

DETAILED DESCRIPTION OF EMBODIMENTS

Overview

Figure 1:
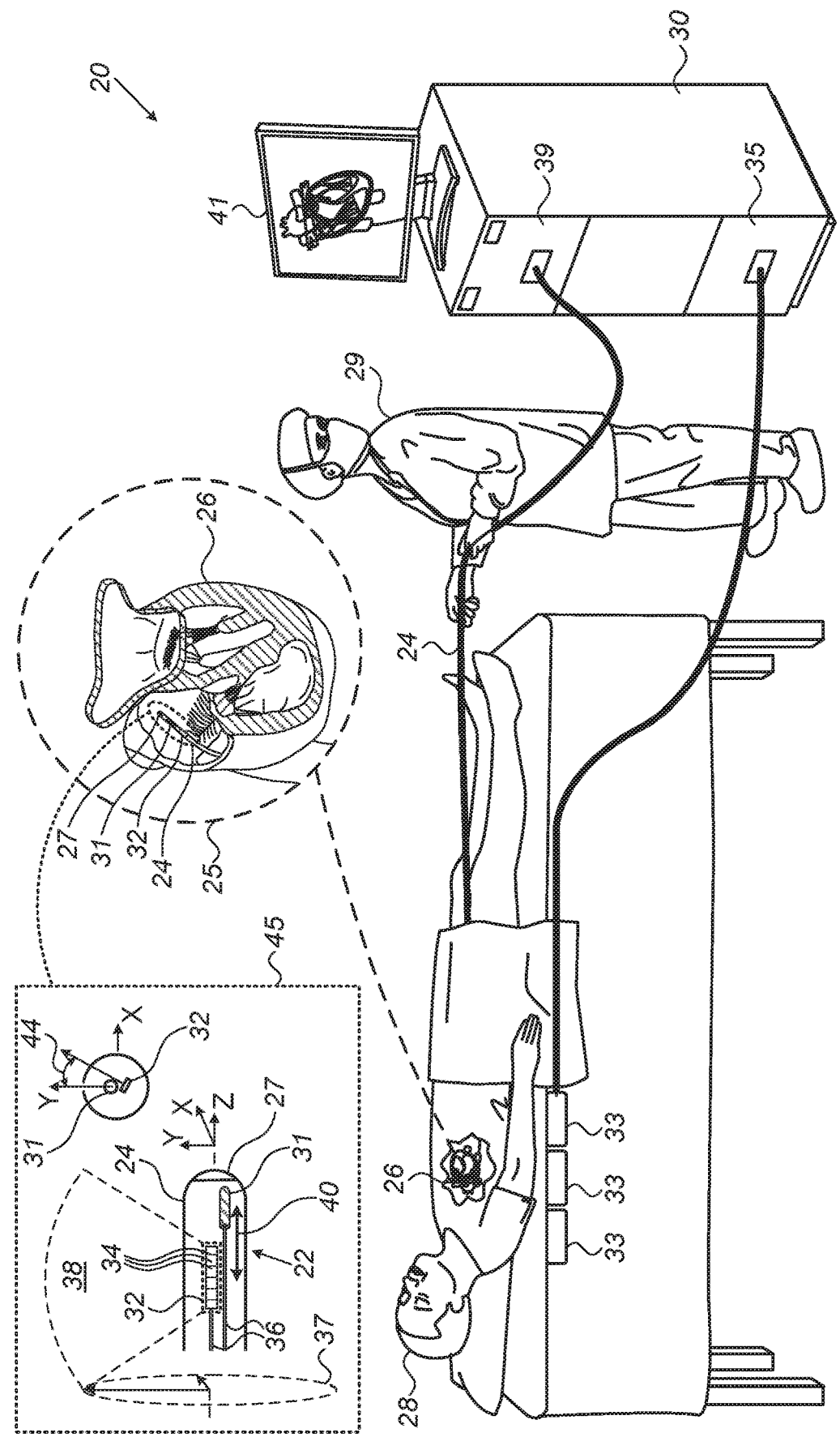
FIG. 1 is a schematic, pictorial illustration of a catheter-based system for ultrasound imaging and position tracking, in accordance with an embodiment of the present invention.

Embodiments of the present invention that are described hereinafter provide improved methods and apparatus for calibrating a probe, such as a catheter, which includes in its distal end an acoustic imaging device and a magnetic position sensor. The acoustic (e.g., ultrasound) imaging device and the magnetic sensor are calibrated in separate steps, within their own, distinct, coordinate systems. To correlate locations measured using both sensors, a registration of the coordinate systems of the ultrasound imaging device with that of the magnetic position sensor is performed in a single apparatus.

An example of such a catheter is the Soundstar® catheter, produced by Biosense-Webster, Inc. (Irvine, Calif.), which comprises both an ultrasonic array producing an ultrasound fan (i.e., have an ultrasonic beam plane), and a magnetic position sensor, at its distal end. With the Soundstar® catheter, both the ultrasonic and magnetic frames of reference (i.e., coordinate systems) should be calibrated and registered with each other.

Embodiments of the present invention provide an acoustic calibration apparatus, which comprises an acoustic phantom, and associated methods. The acoustic phantom comprises continuous "acoustic targets." Acoustic targets are defined hereinafter as physical objects that have known geometries and positions, and reflect well ultrasound waves (i.e., appear in images as high contrast objects). In some embodiments, the acoustic targets are shaped as arcs. The arcs are positioned so as to appear as dots when imaged by the ultrasound imaging device, enable automatic identification of the targets, automatic calibration, and subsequent automatic analysis of the ultrasound imaging device using image processing techniques.

In an embodiment, some of the arcs are aligned orthogonal to the ultrasound beam plane, whereas some of the arcs are aligned slanted relative to the beam plane. The slanted arcs provide means for measuring an angular displacement between the magnetic sensor and the ultrasound coordinate systems, as described below. The slanted targets can also be used for assessing the angular resolution of the imaging device.

In some embodiments, the acoustic phantom is made entirely of non-ferromagnetic materials, and therefore is suitable for use in conjunction with a magnetic calibration apparatus. In this manner calibrations and registration are made in a single apparatus, as described below. In some embodiments, a calibration process of the position sensor provides calibration factors for use in computing coordinates applicable to ultrasound images formed by the probe based on readings of the position sensor. In some embodiments, the calibration factors are used for determining a physical displacement along a longitudinal axis of the probe, between the magnetic sensor and the acoustic imaging device.

By using the disclosed non-ferromagnetic acoustic phantom, tasks such as magnetic calibration, ultrasound calibration and registration of ultrasound coordinates with magnetic coordinates, can all be performed at the same time within a single calibration apparatus. The disclosed calibration phantom, and the disclosed methods of calibration and registration, provide results that are accurate and robust (i.e., preventive of, and tolerant to, potential user errors), are repeatable, and require only a short time to achieve. Improving the calibration and registration processes of cardiac catheters equipped with ultrasound and magnetic sensors may yield more accurate multi-sensor cardiac positioning and mapping systems.

System Description

FIG. 1 is a schematic, pictorial illustration of a catheter-based system 20 for ultrasound imaging and position tracking, in accordance with an embodiment of the present invention. A physician 29 inserts a catheter 24 through the vascular system of a patient 28 so that the distal end of the catheter enters a chamber of the patient's heart. Physician 29 advances the catheter so that an end section of the catheter engages endocardial tissue at a desired location or locations in a heart 26. Catheter 24 is connected by a suitable connector at its proximal end to a console 30.

The console optionally comprises an RF generator 39 for applying RF energy through an electrode 27 (seen in an inset 25 at the distal edge of the distal section of the catheter) in order to ablate the tissue contacted by the distal section. Alternatively or additionally, catheter 24 may be used for other diagnostic and/or therapeutic functions, such as intracardiac electrical mapping or other types of ablation therapy.

In the pictured embodiment, system 20 uses magnetic position sensing to determine position coordinates of the end section of the catheter inside heart 26. To determine the position coordinates, a driver circuit 35 in console 30 drives field generators 33 to generate magnetic fields within the body of patient 28. Typically, field generators 33 comprise coils, which are placed below the patient's torso at known positions external to the body. These coils generate magnetic fields in a predefined working volume that contains heart 26.

As shown in inset 25, a magnetic position sensor 31 is fitted within the distal end of catheter 24. Magnetic position sensor 31 generates position and orientation signals in response to the magnetic fields generated by generators 33. The console processes these signals in order to determine the position (location and/or orientation) coordinates of a distal end 22 of catheter 24, and possibly also the deformation of the end section. Console 30 may use the position coordinates in driving a display 41 to show the location and status of the catheter distal end. This method of position sensing is described in detail, for example, in PCT International Publication WO 96/05768, whose disclosure is incorporated herein by reference, and is implemented in CARTO™ systems produced by Biosense Webster Inc. (Ervine, Calif.).

In some embodiments, system 20 comprises an ultrasound imaging subsystem implemented as part of console 30. As shown in inset 25, the ultrasound imaging subsystem uses an ultrasound imaging device 32 that is fitted in distal end 22 of catheter 24 for imaging the vicinity of the catheter distal end. Ultrasound imaging device 32 is driven with suitable electrical signals by a signal generator (not shown) included in console 30. In response to these signals, ultrasound imaging device 32 emits ultrasound waves that irradiate an intracardiac volume surrounding the distal end of catheter 24. Ultrasound imaging device 32 receives the ultrasound energy reflected from sonically irradiated cardiac tissue and converts the reflected wave to electrical signals. An example of catheter configurations of this sort is the Soundstar® catheter described above. The ultrasound imaging subsystem may display the acquired ultrasound images on display 41.

An inset 45 shows an enlarged, cross-sectional view of distal end 22 of catheter 24. As seen, ultrasound imaging device 32 is proximally adjacent to magnetic position sensor 31. In some embodiments, ultrasound imaging device 32 typically comprises a one-dimensional phased array of transducers 34, which is operated, as is known in the art, so as to create a two-dimensional image "fan" 38 in the plane of the scanning ultrasonic beam (referred to herein as the "beam plane" or "image plane"), which contains the longitudinal axis of the catheter (identified as the Z-axis in the figures). The transducers detect ultrasonic waves that are reflected from objects in the beam plane, and output signals in response to the reflected waves. Typically, these signals are processed by console 30 in order to form and display ultrasound images. Alternatively or additionally, ultrasound transducers 34 may be used for other diagnostic purposes, such as Doppler measurements, or for therapeutic uses.

In some embodiments, ultrasound imaging device 32 comprises a two-dimensional phased array of transducers (device not shown) that are distributed circumferentially around the axis of catheter 24. Such a two-dimensional array is configured to transmit ultrasound waves at respective radial directions, and detect respective ultrasound reflections, over at least part of an entire circumference 37. In such a case, a volumetric section of a cardiac chamber is acquired at each scanning step, where the volumetric section may cover up to a full 360 degrees along the x-y plane (section not illustrated). Such a two-dimensional ultrasound phased array is described in U.S. patent application Ser. No. 15/792,404, filed Oct. 24, 2017, entitled "Determining balloon catheter contact with anatomy using ultrasound," which is assigned to the assignee of the present patent application and whose disclosure is incorporated herein by reference.

Inset 45 shows magnetic position sensor 31 inside distal end 22 of catheter 24, which, as noted above, generates signals that are indicative of a position and orientation of distal end 22 within the body. Based on the position signals that sensor 31 generates, console 30 determines the location and orientation of each fan image captured by ultrasound imaging device 32. Position sensor 31 is typically adjacent to ultrasound imaging device 32 in a fixed locational and orientational relationship. The console is thus able to determine the coordinates of objects appearing in the fan image, as elaborated below.

As shown in inset 45, due to physical constraints in the construction of catheter 24, position sensor 31 and ultrasound imaging device 32 are located in distal end 22 at certain respective distances from the distal tip of the catheter. (This configuration of the position sensor and imaging device is shown by way of example, and the principles of the present invention may similarly be applied to other arrangements of these elements, including side-by-side arrangements.)

The actual position of fan 38 is computed by calibrating a longitudinal displacement 40 between position sensor 31 and the ultrasound imaging device 32, shown in inset 45. The actual orientation of fan 38 is computed by calibrating an angular displacement 44 of fan 38 relative to a reference plane, such as the YZ plane, as further shown in inset 45.

It has been found empirically that, due to deviations in the process of manufacturing catheter 24, the longitudinal and angular displacements typically vary from one catheter to another. Furthermore, the axes of position sensor 31 and of the ultrasonic transducer array in imaging device 32 may not be precisely aligned with the Z-axis or with one another, thereby introducing an additional variation in determining the orientation of fan 38.

Other exemplary calibration systems that combine ultrasonic imaging with magnetic position sensing, as well as the sources of alignment variation noted above, and others, are described in U.S. Pat. Nos. 6,690,963, 6,716,166 and 6,773,402, whose disclosures are incorporated herein by reference.

If not calibrated, the misalignments described above cause errors in determined position coordinates of objects appearing in image fan 38. Certain methods for calibrating and correcting for these alignment variations are described in U.S. Pat. No. 7,090,639, while other methods are described in U.S. Pat. No. 7,874,987, whose disclosures are all incorporated herein by reference. Catheter 24 can be calibrated using system 20 or a dedicated calibration console (not shown).

Although FIG. 1 shows a particular system configuration, other system configurations may be used in alternative embodiments of the present invention. For example, catheter 24 may comprise any other suitable type of position sensor known in the art, such as other types of field sensing devices, e.g., a Hall Effect sensor. Alternatively, sensor 31 may generate magnetic fields, which are detected by sensing antennas outside the body. The principles of the present invention are applicable to substantially any position-sensing technology that can be implemented in a medical probe.

The methods described hereinbelow may be applied using position sensors of other types, such as impedance-based or ultrasonic position sensors. The term "position sensor" as used herein refers to an element mounted on or in catheter 24 that causes console 30 to receive signals indicative of the coordinates of the element. The position sensor may thus comprise a receiver in the catheter, which generates a position signal to the control unit based on energy detected by the sensor; or it may comprise a transmitter that emits energy that is sensed by a receiver external to the probe.

Furthermore, the methods described hereinbelow may similarly be applied in mapping and measurement applications using not only catheters, but also probes of other types, both in the heart and in other body organs and regions.

Acoustic Phantom and Method for Intracardiac Ultrasound Localization Catheter

Figure 2:
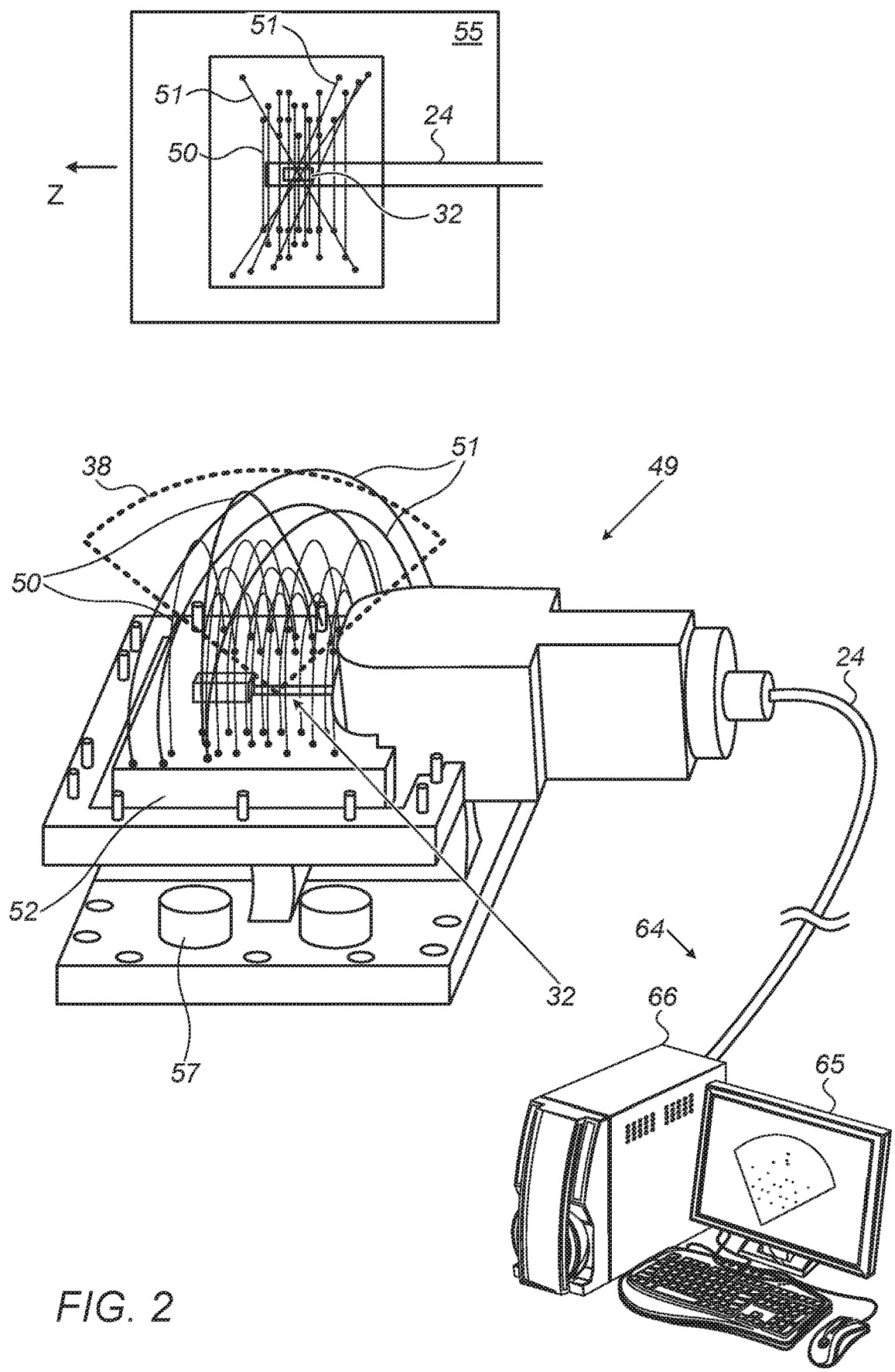
FIG. 2 is a schematic, pictorial illustration of an acoustic phantom coupled with a catheter requiring calibration, and a calibration console, in accordance with an embodiment of the present invention.

FIG. 2 is a schematic, pictorial illustration of an acoustic calibration phantom 49 coupled with a catheter 24 requiring calibration, and a calibration console 64, in accordance with an embodiment of the present invention. In the present example, phantom 49 is made entirely of non-ferromagnetic materials to enable its use in a magnetic calibration apparatus, as further described below.

In some embodiments, distal end 22 of catheter 24 is inserted into a suitable mount 52 that includes one or more fixtures to guide ultrasound imaging device 32 to a given position within phantom 49, as described below. For performing the calibrations, calibration console 64 is used, which typically comprises a processor 66 with suitable signal processing and user interface circuits. As seen, processor 66 is coupled to receive signals from catheter 24. Typically, console 64 enables a user to observe and regulate the functions of catheter 24 and displays on a monitor (display) 65 ultrasound images of acoustic targets that are imaged using the catheter.

The design of acoustic phantom 49 features high tolerance to potential operator errors in catheter positioning during the calibration process. Screws 57 are used to secure phantom 49 inside a magnetic calibration apparatus (described below) that can calibrate magnetic sensor 31 as well.

FIG. 2 shows a set of circular acoustic target arcs that half-encircle ultrasound imaging device 32. Additional slanted acoustic target arcs 51 are seen as well. The various arcs may be made of any suitable ultrasound-reflecting material that is not ferromagnetic. The arrangement of the various arcs is further illustrated in an inset 55, showing a top view of calibration phantom 49. As seen, ultrasound imaging device 32 is held in an approximately "centered" position, due to the mechanical design of phantom 49, meaning that various target arcs 50 and slanted target arcs 51 create half circles about an origin overlapping the positioned ultrasound imaging device 32. However, centering ultrasound imaging device 32 is not required by the disclosed calibration method.

In some embodiments, the cross section of arcs 50 and 51 is circular (i.e., a filled circle). In alternative embodiments, the cross section of the arcs is optimized to improve arc location accuracy. For example, in an embodiment, arcs 50 and 51 comprise a V-shape cross section.

As seen in FIG. 2, target arcs 50 lie in planes (i.e., aligned) orthogonal to the Z direction (the longitudinal axis of catheter 24) and are therefore scanned orthogonally by fan 38. In other words, arcs 50 are aligned so as to continuously intersect an ultrasonic beam plane perpendicularly, such as of fan 38 emitted by ultrasound imaging device 32. In this way, any location on arcs 50 would appear as a circular dot on an ultrasound image including that location, as further illustrated below. Slanted arcs 51, in contrast, form an angle with fan 38. Correspondingly, imaged locations on slanted arcs 51 would appear on an ultrasound images as elliptical dots. Slanted arcs 51 provide means to assess the angle between the ultrasound fan and a reference plane, such as the YZ plane shown in FIG. 1.

The angle between the slanted arc and the Z axis is optimized so as to achieve sufficient angular resolution, while keeping the image spot sufficiently small to maintain location identification accuracy. Other parameters that influence on the angular assessment include arc radius, arc cross section shape, arc cross section diameter, arc material, arc slanted angle, "shadowing" by other "fix" arcs.

The example illustration shown in FIG. 2 is chosen purely for the sake of conceptual clarity. The type and arrangement of acoustic targets may vary, including, for example, intermittent (i.e., discrete) targets, in addition to continuous arcs. Acoustic phantom 49 may be made of various materials, including ferromagnetic metals—if the acoustic calibration is not performed in conjunction with a magnetic calibration apparatus.

Figure 3:
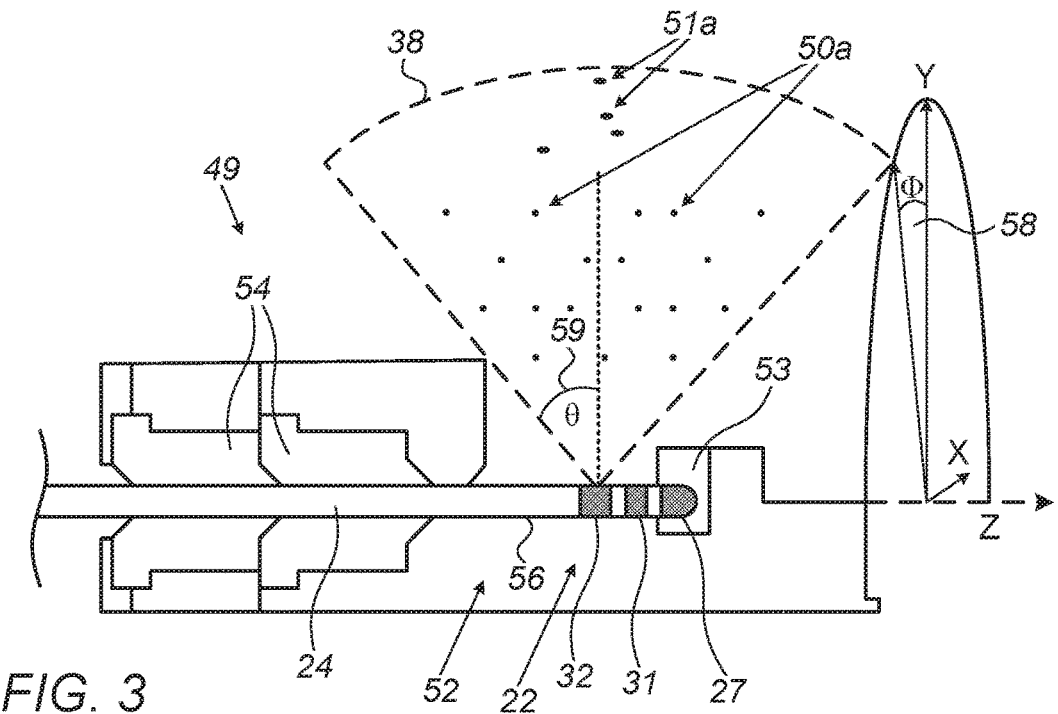
FIG. 3 is a cross-sectional side-view of the acoustic calibration phantom from FIG. 2, in accordance with an embodiment of the present invention.

FIG. 3 is a cross-sectional side-view of acoustic calibration phantom 49 from FIG. 2, in accordance with an embodiment of the present invention. As seen, distal end 22 of catheter 24 is inserted within mount 52 up to a point defined by a stopper 53. Fixtures 54 and a guide 56 ensure distal end 22 is held precisely at that point, while the user may adjust its angle of rotation about the longitudinal axis of distal end 22 by an orientation angle $\phi$ 58. By the adjustment of distal end 22, the orientation of fan 38 may be adjusted to be perpendicular to base 52 (i.e., at $\phi=0$ degrees). By rotation of the catheter, fan 38 may be tilted toward base 52 in both directions, covering a range of orientation angles approximately up to $\phi=\pm 90$ degrees. The acoustic targets are arranged to continuously intersect the ultrasonic beam plane over the given range of observation angles $\theta$ and orientation angles $\phi$.

Guide 56 may comprise a trench, a groove, or any other suitable means to direct, center, and secure distal end 22 of catheter 24. Mount 52 provides a horizontal XZ framework to which arcs 50 and 51 are fixed, while being vertically aligned relative to mount 52, i.e., arcs 50 and 51 are embedded in various planes orthogonal to the XZ plane and cross an origin defined by the designated location in phantom 49 of ultrasound imaging device 32.

As FIG. 3 shows, the numerous target arcs 50 and slanted arcs 51 appear in an ultrasound image as circular dots 50*a* and elliptical dots 51*a*, respectively. These ultrasound images are produced at console 64 and presented on display 65. The dots enable the calibration system to perform the necessary calibrations, as well as derive other results automatically by means of image processing. For example, the spatial resolution that ultrasound imaging device 32 provides at numerous directions can be derived using arcs 50 and 51.

The example illustration shown in FIG. 3 is chosen purely for the sake of conceptual clarity. Some arcs may, for example, be slanted in additional directions. Other mechanical designs of fixtures, actuators, and additional mechanical elements of phantom 49 and respective alignment techniques will occur to a person skilled in the art.

Figure 4:
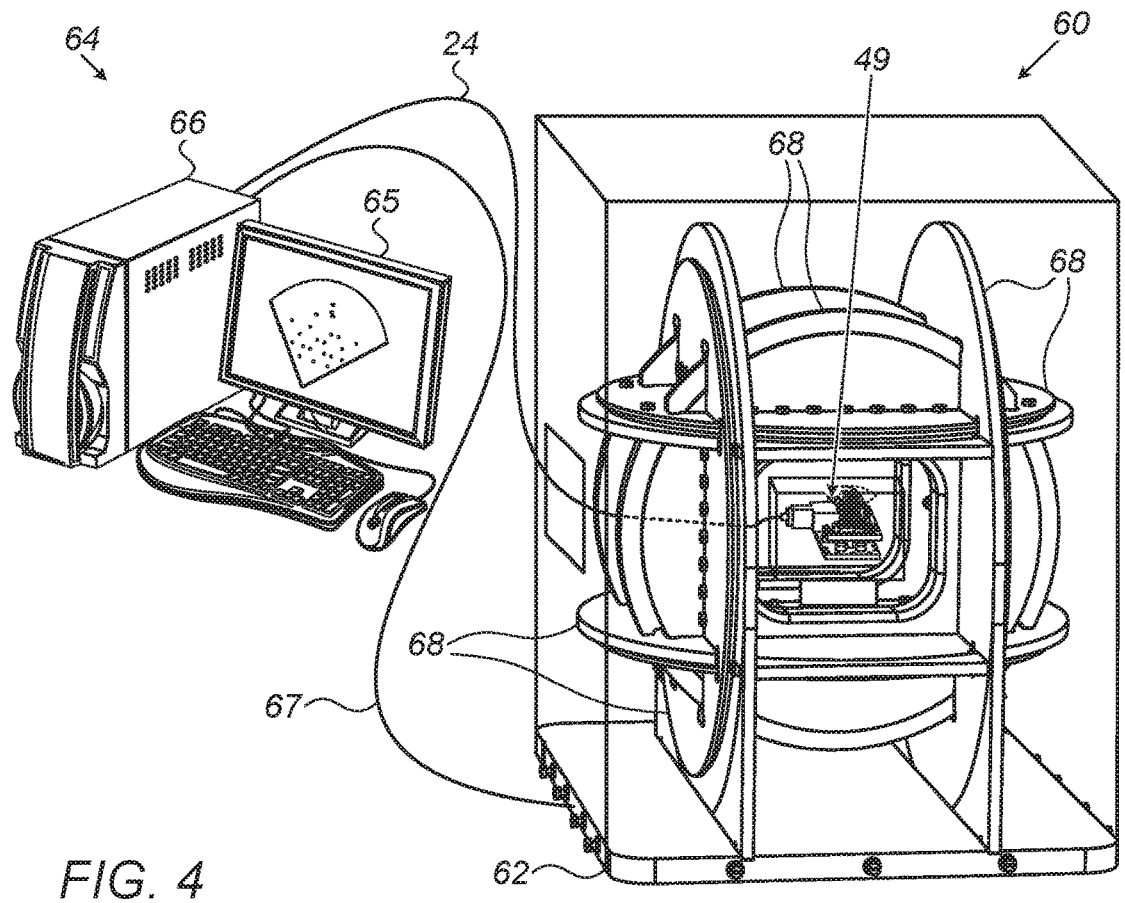
FIG. 4 is a schematic, pictorial illustration of an apparatus for calibration of an ultrasonic imaging catheter, in accordance with an embodiment of the present invention.

FIG. 4 is a schematic pictorial illustration of an apparatus 60 for calibration of an ultrasonic imaging catheter, in accordance with an embodiment of the present invention. Apparatus 60 comprises a base 62, which serves as a rigid mechanical framework for a set of magnetic field generators 68 and acoustic phantom 49. In this embodiment, the field generators comprise three mutually orthogonal pairs of Helmholtz coils 68. Apparatus 60 is connected to calibration console 64, described above, which is now additionally used for driving Helmholtz coils 68 via a cable 67. Based on position signals that sensor 31 generates in response to magnetic fields emitted by coils 68, processor 66 determines the location and orientation of each fan image captured by imaging device 32. The console is thus able to determine coordinates of phantom arc targets 50 and 51, appearing as dots in the fan image. As noted above, distal end 22 of catheter 24 is inserted into a suitable alignment fixture. The alignment is such that position sensor 31 is placed in proximity to the center of the coils (i.e., at the center of field generators 68), with ultrasound imaging device 32 facing toward the target arcs 50 and 51.

In the present embodiment, processor 66 receives the location readings of position sensor 31 in proximity to the center of a Helmholtz cell, with typical position accuracy of 0.1 mm. Position sensor 31 generate these readings in response to gradient-calibrated electromagnetic fields generated by the three pairs of Helmholtz coils 68, as directed from console 64. Console 64 drive each pair of Helmholtz coils with currents running in opposite directions, so that the electromagnetic field in the center has a near-constant gradient. Because the three pairs of Helmholtz coils are orthogonal to one another, the three electromagnetic fields have gradients in the three orthogonal directions.

Before calibrating catheter 24, console 64 is used for calibrating the Helmholtz electromagnetic fields using a mechanically-accurate sensor at known points in the volume that will be used for calibrating the catheter position sensor. The measured positions are referred to a predefined mechanical origin, which is fixed in the frame of reference of base 62. From these measurements, processor 66 accurately maps the Helmholtz electromagnetic field as a function of location. When catheter magnetic sensor 31 is then placed in the calibrated volume, processor 66 may calculate the position and orientation of magnetic sensor 31 to an accuracy of 0.1 mm, which typically exceeds the operational accuracy of the electromagnetic tracker system used in actual operation of catheter 24. This high accuracy is due to the high gradient present in the Helmholtz chamber.

As noted above, the entire set of ultrasonic calibrations and characterizations can be performed while phantom 49 is positioned within apparatus 60. Applying ultrasound calibration and magnetic calibrations in the same set-up enables processor 66 to perform highly accurate registration of the coordinate systems of each of the modalities. This accuracy is manifested by finding an exact longitudinal displacement 40 between the origins of the ultrasonic and magnetic coordinate systems. These origins are typically defined as the center of the transducer array of imaging device 32 and the center of position sensor 31, respectively.

Some embodiments of apparatus 60 and related magnetic calibration methods, as well as methods of registration between the ultrasonic and magnetic coordinate systems, are described in U.S. Pat. Nos. 6,266,551, 7,090,639, 7,874,987 and 7,996,057, whose disclosures are all included herein for reference.

Figure 5:
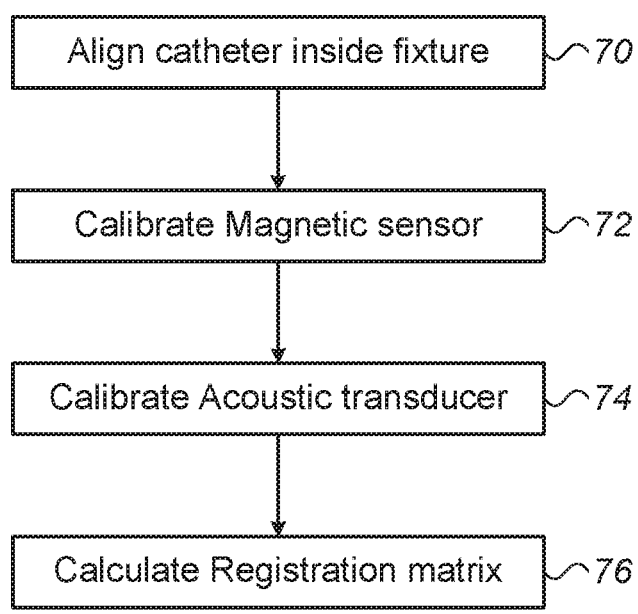
FIG. 5 is a flow chart that schematically illustrates a method for calibrating an intracardiac ultrasound localization catheter, in accordance with an embodiment of the present invention.

FIG. 5 is a flow chart that schematically illustrates a method for calibrating an ultrasonic probe, such as catheter 24, in order to correct for alignment variations, in accordance with an embodiment of the present invention. Initially, distal end 22 of catheter 24 is mechanically aligned in apparatus 60, at a catheter alignment step 70. Using stopper 53, imaging device 32 is brought to a location where fan 38 is centered longitudinally (i.e., along Z-axis) at the origin of the XYZ coordinates.

Once the catheter has been properly positioned at step 70, magnetic position sensor 31 is calibrated, at a position sensor calibration step 72.

Next, ultrasound imaging device 32 is calibrated, at an acoustic transducer calibration step 74, so as to assess (a) the longitudinal displacement 40 between ultrasound imaging device 32 and position sensor 31, and (b) the angular displacement 44 between the ultrasonic beam and a YZ reference plane.

Based on the results of steps 72 and 74 (in whichever order steps 72 and 74 are carried out), processor 66 calculates calibration factors for position sensor 31, for use in computing coordinates applicable to ultrasound images formed by ultrasound imaging device 32 based on readings of position sensor, at a Registration-matrix calculation step 76. The aforementioned coordinates found by ultrasound imaging device 32 belong to high contrast dots appearing in the ultrasound images of target arcs 50 and 51. The calibration factors are used for determining a longitudinal displacement 40 and angular displacement 44. The calibration factors are used subsequently by console 30 in determining the correct position and orientation of fan 38, based on position readings provided by sensor 31, and in finding the correct position and orientation coordinates of objects seen in the fan image.

The example flow chart shown in FIG. 5 is chosen purely for the sake of conceptual clarity. In alternative embodiments, other probes, for example one having a two-dimensional ultrasound array, may be calibrated by the same method, which may involve additional steps, such as verifying coverage of the ultrasound beam over a range of orientation angles $\phi$.

Other functional parameters of ultrasound imaging device 32 and of the ultrasound imaging system as a whole can be characterized. For example, system 20 can verify that the ultrasound images are not geometrically distorted, by means of a processor that checks that the distribution of circular dots 50a and elliptical dots 51a on the images correctly represent the physical arrangement of arcs 50 and 51.

Although the embodiments described above refer specifically to catheter 24, the principles of the present invention are equally applicable to other types of ultrasound probes, including both invasive probes and probes used outside the body.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus for calibration, comprising:
   a mount, which is adapted to hold a medical probe, which comprises an acoustic imaging device that emits ultrasonic beam in a plane, while permitting an orientation of the plane of the ultrasonic beam to be adjusted; and
   one or more acoustic targets, which are arranged to intersect the plane of the ultrasonic beam over a given range of orientation angles,
   wherein the acoustic targets comprise intermittent acoustic targets,
   wherein the acoustic targets are shaped as arcs, the arcs being open curves, wherein the arcs are positioned so as to appear as dots when imaged by the ultrasound imaging device, wherein the arcs enable automatic identification of the targets, automatic calibration, and subsequent automatic analysis of the ultrasound imaging,
   wherein some of the arcs are aligned orthogonal to the ultrasonic beam, wherein some of the arcs are aligned slanted relative to the ultrasonic beam,
   wherein the arcs that are aligned slanted relative to the ultrasonic beam are adapted to be used for assessing an angular resolution of the imaging device; and wherein each arc has a first end and a second end, the first end and second end disposed on an upper surface of the mount, so that each arc is disposed to half-encircle the medical probe;
wherein the mount has the upper surface which is a planar surface, the medical probe and arcs extending over the planar surface such that the ultrasonic beam emits up to the arcs and the open curves face the mount and medical probe.

2. The apparatus according to claim 1, wherein the mount and the acoustic targets are entirely non-ferromagnetic.

3. The apparatus according to claim 1, wherein the probe includes a magnetic position sensor, and wherein the apparatus comprises a position sensor calibration setup, which is adapted to determine, based on readings of the position sensor, a physical displacement along a longitudinal axis of the probe between the magnetic sensor and the acoustic imaging device.

4. A method for producing a calibration apparatus, the method comprising:
providing a mount, which is adapted to hold a medical probe, which comprises an acoustic imaging device that emits ultrasonic beam in a plane, while permitting an orientation of the plane of the ultrasonic beam to be adjusted; and
coupling to the mount one or more acoustic targets, which are arranged to intersect the plane of the ultrasonic beam over a given range of orientation angles,
wherein the acoustic targets comprise intermittent acoustic targets,
wherein the acoustic targets are shaped as arcs, the arcs being open curves, wherein the arcs are positioned so as to appear as dots when imaged by the ultrasound imaging device, wherein the arcs enable automatic identification of the targets, automatic calibration, and subsequent automatic analysis of the ultrasound imaging,
wherein some of the arcs are aligned orthogonal to the ultrasonic beam, wherein some of the arcs are aligned slanted relative to the ultrasonic beam,
wherein the arcs that are aligned slanted relative to the ultrasonic beam are adapted to be used for assessing an angular resolution of the imaging device; and
wherein each arc has a first end and a second end, the first end and second end disposed on an upper surface of the mount, so that each arc is disposed to half-encircle the medical probe;
wherein the mount has the upper surface which is a planar surface, the medical probe and arcs extending over the planar surface such that the ultrasonic beam emits up to the arcs and the open curves face the mount and medical probe.

5. The method according to claim 4, wherein the mount and the acoustic targets are entirely non-ferromagnetic.

6. The method according to claim 4, wherein the probe includes a magnetic position sensor, and comprising coupling to the mount and the acoustic targets a position sensor calibration setup, which is adapted to determine, based on readings of the position sensor, a physical displacement along a longitudinal axis of the probe between the magnetic sensor and the acoustic imaging device.

7. A method for calibration, comprising:
holding a medical probe, which comprises an acoustic imaging device that emits ultrasonic beam in a plane, in a mount, while permitting an orientation of the plane of the ultrasonic beam to be adjusted; and
calibrating the acoustic imaging device using one or more acoustic targets, which are arranged to continuously intersect the plane of the ultrasonic beam over a given range of orientation angles;
wherein at least one of the one or more acoustic targets is an arc, the arc being an open curve having a first end and a second end, the first end and second end disposed on an upper surface of the mount, so that the arc is disposed to half-encircle the medical probe;
wherein the mount has the upper surface which is a planar surface, the medical probe and arc extending over the planar surface such that the ultrasonic beam emits up to the arc and the open curve faces the mount and medical probe.

* * * * *